United States Patent [19]
O'Lenick, Jr. et al.

[11] Patent Number: 5,854,319
[45] Date of Patent: Dec. 29, 1998

[54] REACTIVE SILICONE EMULSIONS CONTAINING AMINO ACIDS

[75] Inventors: Anthony J. O'Lenick, Jr., Lilburn, Ga.; Charles W. Buffa, Teaneck, N.J.

[73] Assignees: Lambent Technologies Inc, Norcross, Ga.; Biosil Technologies Inc, Paterson, N.J.

[21] Appl. No.: 565,407

[22] Filed: Nov. 30, 1995

[51] Int. Cl.$^6$ ...................................... C08L 89/00
[52] U.S. Cl. ............................ 524/17; 524/236; 524/704; 524/714
[58] Field of Search .............................. 524/837, 17, 704, 524/714, 236

[56] References Cited

U.S. PATENT DOCUMENTS 5,260,055  11/1993  Imperante et al. ..................... 424/71
5,378,787   1/1995  Vrckovnik et al. ..................... 528/14

*Primary Examiner*—Melvyn I. Marquis

[57] ABSTRACT

The present invention relates to a composition, process for preparation and use of a novel emulsion composition in the personal care industry. The composition when applied to hair provides outstanding lubrication, and delivers amino acids or proteins to the hair fiber. This aides in the manageability of the hair and remediates damage from treatment processes like permanent waving, dying and relaxing of the hair as well as environmental effects upon the hair.

9 Claims, No Drawings

REACTIVE SILICONE EMULSIONS CONTAINING AMINO ACIDS

DESCRIPTION OF THE ART AND PRACTICES

Silicone oils (dimethylpolysiloxane) have been known to be active at the surface of plastic, cellulosic and synthetic fibers as well as hair. Despite the fact that they are lubricants that are stable to oxidation, their high cost and lack of durability has made them cost prohibitive in most application areas.

The low efficiency of silicone oils is due to the fact that the oil is very water insoluble. Emulsions are generally prepared which contain silicone dispersed in micelles. While this method of application is easier for processing, much of the oil stays in the surfactant micelle and never gets deposited on the fiber. That which does deposit on the fiber surface remains there by hydrophobic binding, not ionic bonding. Since the polydimethylsiloxane is not in an ionic bonded the effect is very transient. The product is removed with one washing.

It is highly desirable to be able to deliver a silicone to the surface of the hair in a stable aqueous composition which will upon drying polymerize on the hair making a crosslinked network and one which will react an amino acid or protein to the hair's surface as part of the silicone matrix. It was not until the compounds of the present invention that this was possible.

THE INVENTION

The present invention relates to a composition, process for preparation and use of a novel emulsion composition in the personal care industry. The composition when applied to hair provides outstanding lubrication, and delivers amino acids or proteins to the hair fiber. This aides in the manageability of the hair and remediates damage from treatment processes like permanent waving, dying and relaxing of the hair as well as environmental effects upon the hair.

The compositions of the present invention are emulsions. These emulsions are applied to the hair surface preferably in a conditioner. The emulsion breaks causing the deposition of a uniform coating of composition of the current invention.

The emulsion composition is reactive after the water is removed. The composition is made up of a silanol, a alkoxy silicone and a nitrogen containing material, preferably an amino compound. The amino compound catalyses the reaction between the silanol hydroxyl group, the alkoxy group and the amino group. The result is a highly branched covalently bonded amino functional silicone polymer.

The compositions of the present invention are stable emulsions. These emulsions are applied to the hair surface whereupon they polymerize on the hair and provide conditioning and delivery of amino acids to the hair.

OBJECT OF THE INVENTION

It is the objective of the present invention to provide a composition which is a stable emulsion containing (a) a silanol, (b) an alkoxy silicone crosslinking agent, (c) a water soluble amino compound, preferably an amino acid or protein, (d) an emulsifier and (e) water. The composition polymerizes upon dry down. The silanol is the linear source of silicone, the alkoxy silicone compound provides crosslinking, the amino compound is the necessary catalyst for the reaction, the emulsifier is needed to provide a stable emulsion, and water is necessary as a diluting solvent, so that the polymerization does not occur before contact with the hair.

It is also another objective of the invention o provide a process for treating the hair which comprises the contacting of the hair with an effective conditioning amount of the above composition, allowing the contacted hair to dry and in a preferred embodiment, applying heat from a blow drier to accelerate the crosslinking.

SUMMARY OF THE INVENTION

The invention discloses a stable emulsion containing (a) a silanol, (b) an alkoxy silicone crosslinking agent, (c) a water soluble amino compound, preferably an amino acid or protein, (d) an emulsifier and (e) water. The composition polymerizes upon dry down. The silanol is the linear source of silicone, the alkoxy silicone provides crosslinking, the amino compound is the necessary catalyst for the reaction, the emulsifier is needed to provide a stable emulsion, and water is necessary as a diluting solvent, so that the polymerization does not occur before contact with the hair.

DETAILED DESCRIPTION OF THE INVENTION

The compositions of the present invention are made up of the following critical components:

a) an alkoxy silicone compound conforming to the following structure:

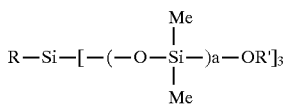

Me is methyl;
R is alkyl having one to ten carbon atoms;
R' is methyl or ethyl;
a is an integer ranging from 1 to 12.

b) A silanol conforms to the following structure:

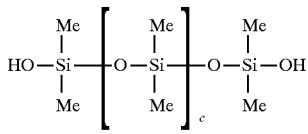

Me is methyl and a ranges from 1 to 2,000.

3) An amino compound

The amino source of choice is an amino acid, or a protein. Proteins are materials which play a critical role in all biological processes. They are natural products and have enjoyed increasing use in personal care products as conditioners, humectants and softeners. Natural proteins, which are high molecular weight polymers, are generally hydrolyzed into lower molecular weight proteins to obtain water solubility. The water solubility results in easier formulating, but the soluble proteins are less substantive to hair and skin. Consequently, the water soluble proteins end up washed off the substrate being treated. The compounds of the present invention are far more substantive since they have silicone in the molecule. Not only is the silicone more substantive to the skin and hair, the presence of alkylene oxide in the silicone polymer in a preferred embodiment results in a protein with an inverse cloud point. The silicone protein becomes insoluble above this temperature and is more substantive to the hair and skin. This suggests the use of these materials in treatment products were heat is applied, like hot oil treatments.

Amino acids are the basic structural units of proteins. An amino acid has both an amino group and a carboxyl group.

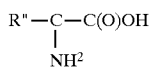

The amino acids are well known to those skilled in the art. They are:

| Amino Acids | | |
|---|---|---|
| Alanine | Arginine | Asparagine |
| Aspartic Acid | Glutamine | Glycine |
| Histidine | Isoleucine | Leucine |
| Lysine | Methionine | Phenylalanine |
| Proline | Serine | Threonine |
| Tryptophan | Tyrosine | Valine |

In proteins the carboxyl group of one amino acid is joined to the carboxyl group of another amino acid in an amide bond. When this aide bond is in a protein it is called a peptide bond. Many amino acids are joined in peptide bonds to form a polypeptide chain. This polypeptide chain is what we commonly call a protein. The polypeptide has a free amino group and a free carboxyl group present.

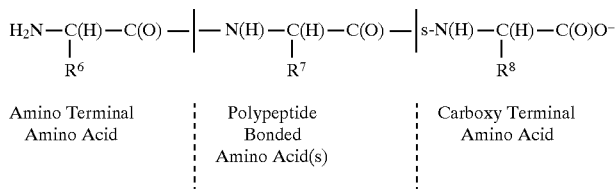

s is an integer from 0 to 5,000, giving the protein a molecular weight up to 500,000 EMWU (EMWU is equivalent molecular weight units)

The compounds of the present invention are dependant upon the reaction of the terminal amino group in the protein with a reactive silicone intermediate which results in functionalizing of the amino group.

It will be clearly understood that the "polypeptide bonded amino acids can be any combination of the amino acids listed above in any order.

4) Emulsifying agent(s)

In a preferred embodiment composition contains a nonionic emulsifier which has a HLB ranging from 8 to 10.

Examples of emulsifiers which are useful are;

| Trade name | HLB | Description |
|---|---|---|
| Neodol 23-3 | 8 | $C_{12}H_{24}O-(CH_2CH_2-O)_3H$ 3 mole ethoxylate |
| Alkasurf DA-3 | 9 | $C_{10}H_{22}O-(CH_2CH_2-O)_3H$ 3 mole ethoxylate |
| Alkasurf NP-5 | 10 | Nonylphenol 5 mole ethoxylate |
| 50/50 blend of Tergitol 15-S-3 and Tergitol 15-S-5 | 9.5 | Secondary Alcohol ethoxylates having three and five moles EO |

NEODOL is a trademark of Shell chemical
ALKASURF is a trademark of Alkaril Chemicals Inc.
TERGITOL is a trademark of Union Carbide Chemical
and
5) Water

EXAMPLES

Raw Materials

The raw materials useful in the preparation of the compounds of the present invention are listed below and have been designated as RM-1 through RM-36. That stands for Raw Material Example 1 through Raw Material Example 36.

1) Alkoxy Silicone Compounds

The silicone compounds useful for the preparation of the compounds of the present invention were provided by Siltech Inc. and conform to the following structures:

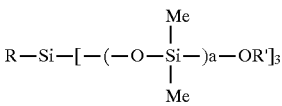

Me is methyl;
R is alkyl having one to ten carbon atoms;
R' is methyl or ethyl;
a is an integer ranging from 0 to 12.

The following compounds are commercially available from Siltech Inc. of Norcross, Ga.;

| Silicone Example | R | R' | a |
|---|---|---|---|
| RM-1 | $CH_3$ | $CH_3$ | 0 |
| RM-2 | $CH_3$ | $CH_2CH_3$ | 8 |
| RM-3 | $CH_3$ | $CH_3$ | 12 |
| RM-4 | $C_4H_9$ | $CH_3$ | 4 |
| RM-5 | $C_4H_9$ | $CH_2CH_3$ | 12 |
| RM-6 | $C_8H_{17}$ | $CH_3$ | 4 |
| RM-7 | $C_8H_{17}$ | $CH_2CH_3$ | 0 |
| RM-8 | $CH_3$ | $CH_3$ | 2 |
| RM-9 | $CH_3$ | $CH_2CH_3$ | 0 |
| RM-10 | $CH_3$ | $CH_3$ | 2 |
| RM-11 | $C_4H_9$ | $CH_3$ | 2 |
| RM-12 | $C_4H_9$ | $CH_2CH_3$ | 0 |
| RM-13 | $C_4H_9$ | $CH_3$ | 0 |
| RM-14 | $C_4H_9$ | $CH_2CH_3$ | 0 |

2) Silanol Compounds

Silanol compounds are well known and are marketed in the trade under many names. The compounds conform to the following generic structure;

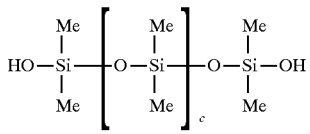

Me is methyl and c ranges from 1 to 2,000.

Compounds conforming to the above structure are available from Siltech Inc. Norcross Ga. and are marketed under the Siltech S series tradename shown;

| Example | Name | Molecular Weight | Value of "c" |
|---------|------------|------------------|--------------|
| RM-15   | Siltech S 700 | 500         | 4            |
| RM-16   | Siltech S 701 | 1,000       | 11           |
| RM-17   | Siltech S 706 | 6,000       | 79           |
| RM-18   | Siltech S 710 | 10,000      | 133          |
| RM-19   | Siltech S 750 | 50,000      | 673          |
| RM-20   | Siltech S 790 | 86,000      | 1160         |
| RM-21   | Siltech S HV  | 150,000     | 2000         |

3) Amino Acids

Examples of Amino acids are:

| Example | Amino Acid |
|---------|------------|
| RM-22   | Alanine |
| RM-23   | Arginine |
| RM-24   | Asparagine |
| RM-25   | Aspartic Acid |
| RM-26   | Glutamine |
| RM-27   | Glycine |
| RM-28   | Histidine |
| RM-29   | Isoleucine |
| RM-30   | Leucine |
| RM-31   | Lysine |
| RM-32   | Methionine |
| RM-33   | Phenylalanine |
| RM-34   | Proline |
| RM-35   | Serine |
| RM-36   | Threonine |
| RM-37   | Tryptophan |
| RM-38   | Tyrosine |
| RM-39   | Valine |

Examples of proteins are:

Proteins useful in the preparation of the products of the present invention are derived from many sources. Many are prepared by the hydrolysis of native proteins. The hydrolysis results in cleavage of some of the polypeptide bonds and increases water solubility. The hydrolysis processes are either acid, alkaline or enzymatic and are well known to those skilled in the art.

Soya Protein (CAS number 68153-28-6); Milk Protein (CAS number 9000-71-9); Wheat Protein; Oat Protein; Vegetable Protein; Keratin Protein (CAS Number 68238-35-7); Placental Protein and Collagen are all sources from which protein is derived.

The proteins useful in the preparation of the compounds of the present invention, in a preferred embodiment range in molecular weight from 1,000 equivalent molecular weight units to 500,000 equivalent molecular weight units. The equivalent molecular weight units are determined by calculation of the free amino groups. An analysis called the "amine value" is run using a standardized acid titrant. The titrations are well known to the fatty chemist and are determined as follows;

$$\text{Amine Value} = \frac{(56.1)\,(\text{normality})\,(\text{ml titrated to pH 5.5})}{(\text{weight in grams of sample})}$$

The amine value is expressed in mg KOH/gm. The amine value is then converted into equivalent molecular weight using the following formula;

$$\text{Equivalent Molecular Weight} = \frac{56,110}{\text{Amine Value (mg KOH/gm)}}$$

| Example Number | Commercial Name | Equivalent weight |
|----------------|-----------------|-------------------|
| RM-40 | Peptin 2,000 | 2,054 EMWU |
| RM-41 | Peptin 5,000 | 5,010 EMWU |
| RM-42 | Polypro 15,000 | 14,980 EMWU |
| RM-43 | Peptin AH | 1,500 EMWU |
| RM-44 | Sollagen | 275,000 EMWU |
| RM-45 | Wheat Protein (Hydrolyzed) | 500 EMWU |
| RM-46 | Wheat Protein | 2,505 EMWU |
| RM-47 | Oat Protein | 5,560 EMWU |
| RM-48 | Soya Protein | 15,625 EMWU |
| RM-49 | Collagen | 500,120 EMWU |
| RM-50 | Placental Protein | 50,450 EMWU |

(Peptin, Polupro, and Sollagen are Trademarks of Hormel)
(Samples obtained from Phoenix Chemical Inc.)

4) Emulsifiers

Examples of emulsifiers which are useful are;

| Example | Trade name | HLB | Description |
|---------|------------|-----|-------------|
| RM-51 | Neodol 23-3 | 8 | $C_{12}H_{24}O$—$(CH_2CH_2$—$O)_3H$ 3 mole ethoxylate |
| RM-52 | Alkasurf DA-3 | 9 | $C_{10}H_{22}O$—$(CH_2CH_2)_3H$ 3 mole ethoxylate |
| RM-53 | Alkasurf NP-5 | 10 | Nonylphenol 5 mole ethoxylate |
| RM-54 | 50/50 blend of Tergitol 15-S-3 and Tergitol 15-S-5 | 9.5 | Alcohol ethoxylates having three and five moles EO |

COMPOUNDS OF THE PRESENT INVENTION

General Procedure

To enough water to adjust the solids to 60% by weight of the total formulation is added the specified amount of surfactants under agitation. Mix well about 15 minutes. Slowly add the specified amount of the specified silanol under good agitation over a one hour period. Slowly add the specified amount of alkoxy silicone over a one hour period. Add the specified amount of the specified amino acid or protein. Mix one hour after all ingredients have been added. Homogenize in a Matin Gaulin Homogenizer at 6,000 psi. Allow to cool under agitation. The resulting emulsion is used as prepared.

The calculation of the amount of water to add is:

A = Weight in grams of (silanol + alkoxy silicone + emulsifier + amino)

Water to Add = (A/0.60) − A

So for example 1;
A=250.0+70.0+5.0+89.0=414.0
Water to Add=(414.0/0.60)−414.0=276.0 gm Emulsions were prepared using the above procedure and the following formulations;

EXAMPLES 1–29

| Ex # | Silanol Type | Grams | Alkoxy Silicone Ex. # | Grams | Emulsifier Ex. # | Grams | Amino Source Ex. # | Grams |
|---|---|---|---|---|---|---|---|---|
| 1 | RM15 | 250.0 | RM1 | 70.0 | RM51 | 5.0 | RM22 | 89.0 |
| 2 | RM16 | 500.0 | RM2 | 1320.0 | RM52 | 5.0 | RM23 | 174.2 |
| 3 | RM17 | 3000.0 | RM3 | 1892.0 | RM53 | 4.0 | RM24 | 132.1 |
| 4 | RM18 | 5000.0 | RM4 | 720.0 | RM54 | 3.0 | RM25 | 133.1 |
| 5 | RM19 | 25000.0 | RM5 | 1920.0 | RM51 | 5.0 | RM26 | 146.1 |
| 6 | RM20 | 43000.0 | RM6 | 786.0 | RM52 | 5.0 | RM27 | 75.0 |
| 7 | RM21 | 7S000.0 | RM7 | 186.0 | RM53 | 5.0 | RM28 | 155.2 |
| 8 | RM15 | 250.0 | RM8 | 120.0 | RM54 | 5.0 | RM29 | 131.2 |
| 9 | RM16 | 500.0 | RM9 | 100.0 | RM51 | 5.0 | RM30 | 131.2 |
| 10 | RM17 | 3000.0 | RM10 | 400.0 | RM52 | 5.0 | RM31 | 146.2 |
| 11 | RM18 | 5000.0 | RM11 | 420.0 | RM53 | 5.0 | RM32 | 149.2 |
| 12 | RM19 | 25000.0 | RM12 | 120.0 | RM54 | 5.0 | RM33 | 165.2 |
| 13 | RM20 | 43000.0 | RM13 | 120.0 | RM54 | 5.0 | RM34 | 115.1 |
| 14 | RM21 | 75000.0 | RM14 | 120.0 | RM52 | 5.0 | RM35 | 105.1 |
| 15 | RM15 | 250.0 | RM14 | 120.0 | RM53 | 5.0 | RM36 | 119.1 |
| 16 | RM16 | 500.0 | RM1 | 70.0 | RM51 | 3.0 | RM37 | 204.3 |
| 17 | RM17 | 3000.0 | RM13 | 120.0 | RM51 | 3.0. | RM38 | 181.9 |
| 18 | RM18 | 5000.0 | RM12 | 80.0 | RM52 | 3.0 | RM39 | 117.1 |
| 19 | RM19 | 25000.0 | RM11 | 280.0 | RM53 | 3.0 | RM40 | 2054.0 |
| 20 | RM20 | 43000.0 | RM10 | 290.0 | RM54 | 3.0 | RM41 | 5010.0 |
| 21 | RM21 | 75000.0 | RM9 | 50.0 | RM51 | 3.0 | RM42 | 14980.0 |
| 22 | RM15 | 250.0 | RM8 | 60.0 | RM52 | 4.0 | RM43 | 1500.0 |
| 23 | RM16 | 500.0 | RM7 | 100.0 | RM53 | 4.0 | RM44 | 275000.0 |
| 24 | RM17 | 3000.0 | RM6 | 395.0 | RM54 | 4.0 | RM45 | 500.0 |
| 25 | RM18 | 5000.0 | RM5 | 1000.0 | RM51 | 4.0 | RM46 | 2505.0 |
| 26 | RM19 | 25000.0 | RM4 | 360.0 | RM52 | 4.0 | RM47 | 5560.0 |
| 27 | RM20 | 43000.0 | RM3 | 946.0 | RM53 | 4.0 | RM48 | 15625.0 |
| 28 | RM21 | 75000.0 | RM2 | 660.0 | RM54 | 4.0 | RM49 | 500120.0 |
| 29 | RM21 | 75000.0 | RM2 | 660.0 | RM54 | 4.0 | RM50 | 50450.0 |

General Procedure

To enough water to adjust the solids to 35% by weight of the total formulation is added the specified amount of surfactants under agitation. Mix well about 15 minutes. Slowly add the specified amount of the specified silanol under good agitation over a one hour period. Slowly add the specified amount of alkoxy silicone over a one hour period. Add the specified amount of the specified amino acid or protein. Mix one hour after all ingredients have been added. Homogenize in a Matin Gaulin Homogenizer at 6,000 psi. Allow to cool under agitation. The resulting emulsion is used as prepared.

The calculation of the amount of water to add is:

A=Weight in grams of (silanol+Alkoxy Silane+Emulsifier+Amino)

Water to Add=(A/0.35)−A

So for example 30;

A=250.0+70.0+5.0+89.0=414.0

Water to Add=(414.0/0.35)−414.0=768.8 gm

Emulsions were prepared using the above procedure and the following formulations;

EXAMPLES 30–59

| Ex # | Silanol Type | Grams | Alkoxy Silicone Ex. # | Grams | Emulsifier Ex. # | Grams | Amino Source Ex. # | Grams |
|---|---|---|---|---|---|---|---|---|
| 30 | RM15 | 250.0 | RM1 | 70.0 | RM51 | 5.0 | RM22 | 89.0 |
| 31 | RM16 | 500.0 | RM2 | 1320.0 | RM52 | 5.0 | RM23 | 174.2 |
| 32 | RM17 | 3000.0 | RM3 | 1892.0 | RM53 | 4.0 | RM24 | 132.1 |
| 33 | RM18 | 5000.0 | RM4 | 720.0 | RM54 | 3.0 | RM25 | 133.1 |
| 34 | RM19 | 25000.0 | RM5 | 1920.0 | RM51 | 5.0 | RM26 | 146.1 |
| 35 | RM20 | 43000.0 | RM6 | 786.0 | RM52 | 5.0 | RM27 | 75.0 |
| 36 | RM21 | 75000.0 | RM7 | 186.0 | RM53 | 5.0 | RM28 | 155.2 |
| 38 | RM15 | 250.0 | RM8 | 120.0 | RM54 | 5.0 | RM29 | 131.2 |
| 39 | RM16 | 500.0 | RM9 | 100.0 | RM51 | 5.0 | RM30 | 131.2 |
| 40 | RM17 | 3000.0 | RM10 | 400.0 | RM52 | 5.0 | RM31 | 146.2 |
| 41 | RM18 | 5000.0 | RM11 | 420.0 | RM53 | 5.0 | RM32 | 149.2 |
| 42 | RM19 | 25000.0 | RM12 | 120.0 | RM54 | 5.0 | RM33 | 165.2 |
| 43 | RM20 | 43000.0 | RM13 | 120.0 | RM54 | 5.0 | RM34 | 115.1 |
| 44 | RM21 | 75000.0 | RM14 | 120.0 | RM52 | 5.0 | RM35 | 105.1 |
| 45 | RM15 | 250.0 | RM14 | 120.0 | RM53 | 5.0 | RM36 | 119.1 |
| 46 | RM16 | 500.0 | RM1 | 70.0 | RM51 | 3.0 | RM37 | 204.3 |
| 47 | RM17 | 3000.0 | RM13 | 120.0 | RM51 | 3.0 | RM38 | 181.9 |
| 48 | RM18 | 5000.0 | RM12 | 80.0 | RM52 | 3.0 | RM39 | 117.1 |
| 49 | RM19 | 25000.0 | RM11 | 280.0 | RM53 | 3.0 | RM40 | 2054.0 |

| Ex # | Silanol Type | Silanol Grams | Alkoxy Silicone Ex. # | Alkoxy Silicone Grams | Emulsifier Ex. # | Emulsifier Grams | Amino Source Ex. # | Amino Source Grams |
|---|---|---|---|---|---|---|---|---|
| 50 | RM20 | 43000.0 | RM10 | 290.0 | RM54 | 3.0 | RM41 | 5010.0 |
| 51 | RM21 | 75000.0 | RM9 | 50.0 | RM51 | 3.0 | RM42 | 14980.0 |
| 52 | RM15 | 250.0 | RM8 | 60.0 | RM52 | 4.0 | RM43 | 1500.0 |
| 53 | RM16 | 500.0 | RM7 | 100.0 | RM53 | 4.0 | RM44 | 275000.0 |
| 54 | RM17 | 3000.0 | RM6 | 395.0 | RM54 | 4.0 | RM45 | 500.0 |
| 55 | RM18 | 5000.0 | RM5 | 1000.0 | RM51 | 4.0 | RM46 | 2505.0 |
| 56 | RM19 | 25000.0 | RM4 | 360.0 | RM52 | 4.0 | RM47 | 5560.0 |
| 57 | RM20 | 43000.0 | RM3 | 946.0 | RM53 | 4.0 | RM48 | 15625.0 |
| 58 | RM21 | 75000.0 | RM2 | 660.0 | RM54 | 4.0 | RM49 | 500120.0 |
| 59 | RM21 | 75000.0 | RM2 | 660.0 | RM54 | 4.0 | RM50 | 50450.0 |

Applications Results

The compounds of the present invention, when applied to the hair and allowed to dry, provide conditioning, softening and improvement to damaged hair.

What is claimed:

1. An emulsion which comprises;

A) an alkoxy silicone compound which conforms to the following structure:

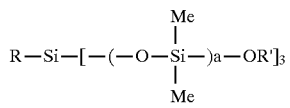

Me is methyl;
R is alkyl having one to ten carbon atoms;
R' is methyl or ethyl;
a is an integer ranging from 1 to 12;

B) a silanol which conforms to the following structure:

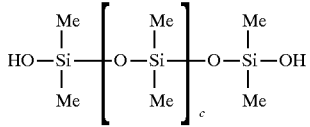

Me is methyl and c ranges from 1 to 2,000;

C) an amino compound selected from the group consisting of amino acids and proteins;
D) an emulsifying agent; and
E) water.

2. An emulsion of claim 1 wherein R is methyl.
3. An emulsion of claim 1 wherein R is octyl.
4. An emulsion of claim 1 wherein said amino compound is a protein.
5. An emulsion of claim 1 wherein said amino compound is an amino acid.
6. An emulsion of claim 1 wherein said emulsifying agent has an HLB ranging from 8 to 10.
7. An emulsion of claim 1 wherein a is 12.
8. An emulsion of claim 1 wherein a is 4.
9. An emulsion of claim 1 wherein R' is methyl.

* * * * *